(12) United States Patent
Weller et al.

(10) Patent No.: US 7,531,588 B2
(45) Date of Patent: May 12, 2009

(54) SILANE COMPOSITIONS, PROCESSES FOR THEIR PREPARATION AND RUBBER COMPOSITIONS CONTAINING SAME

(75) Inventors: Keith J. Weller, Wappingers Falls, NY (US); Lesley Hwang, White Plaines, NY (US); Richard W. Cruse, Yorktown Height, NY (US); Leda Gonzalez, Norwalk, CT (US); Robert J. Pickwell, Tonawanda, NY (US); Martin Hofstetter, Bellrose Manor, NY (US); Wesley E. Sloan, Walkill, NY (US); Prashant G. Joshi, Ossining, NY (US)

(73) Assignee: Momentive Performance Materials Inc., Albany, NY (US)

( * ) Notice: Subject to any disclaimer, the term of this patent is extended or adjusted under 35 U.S.C. 154(b) by 81 days.

(21) Appl. No.: 10/918,828

(22) Filed: Aug. 13, 2004

(65) Prior Publication Data

US 2006/0281841 A1    Dec. 14, 2006

Related U.S. Application Data

(63) Continuation-in-part of application No. 10/903,960, filed on Jul. 30, 2004.

(51) Int. Cl.
  *C08K 5/24* (2006.01)
  *C07F 7/04* (2006.01)

(52) U.S. Cl. .................. 524/263; 524/493; 524/264; 556/413

(58) Field of Classification Search ............ 524/263, 524/264, 493; 556/413
See application file for complete search history.

(56) References Cited

U.S. PATENT DOCUMENTS

| | | | |
|---|---|---|---|
| 2,811,542 A | 10/1957 | Speier et al. | |
| 3,065,254 A | 11/1962 | Silva | |
| 3,159,601 A | 12/1964 | Ashby | |
| 3,159,662 A | 12/1964 | Ashby | |
| 3,220,972 A | 11/1965 | Lamoreaux et al. | |
| 3,249,461 A | 5/1966 | Te Grotenhuis | |
| 3,445,496 A | 5/1969 | Ryan | |
| 3,661,954 A | 5/1972 | Legrow | |
| 3,692,812 A | 9/1972 | Berger | |
| 3,715,334 A | 2/1973 | Karstedt | |
| 3,734,763 A | 5/1973 | Plueddemann | |
| 3,775,452 A | 11/1973 | Karstedt | |
| 3,798,196 A | 3/1974 | Rocktaschel | |
| 3,819,675 A | 6/1974 | Plueddemann | |
| 3,869,340 A | 3/1975 | Kotzsch | |
| 3,922,436 A | 11/1975 | Bell et al. | |
| 3,956,353 A | 5/1976 | Plueddemann | |
| 3,971,883 A | 7/1976 | Meeks et al. | |
| 4,060,539 A | 11/1977 | Seiler et al. | |
| 4,152,347 A | 5/1979 | Pletka et al. | |
| 4,279,449 A | 7/1981 | Martin | |
| 4,574,133 A | 3/1986 | Umpleby | |
| 4,820,751 A | 4/1989 | Takeshita et al. | |
| 5,116,886 A | 5/1992 | Wolff et al. | |
| 5,227,425 A | 7/1993 | Rauline | |
| 5,326,895 A | 7/1994 | Kubota et al. | |
| 5,580,919 A | 12/1996 | Agostini et al. | |
| 5,663,226 A | 9/1997 | Scholl | |
| 5,674,932 A | 10/1997 | Agostini et al. | |
| 6,005,027 A | 12/1999 | Guillet et al. | |
| 6,127,468 A | 10/2000 | Cruse | |
| 6,191,286 B1 | 2/2001 | Gunther et al. | |
| 6,204,339 B1 | 3/2001 | Waldman | |

(Continued)

FOREIGN PATENT DOCUMENTS

AU             730753           7/1997

(Continued)

OTHER PUBLICATIONS

Teng, Zhu et al., "Palladium-induced intramolecular coupling reactions of some alkenyl (2-iodobenzyl)silanes" Helvetica Chimica Acta, 82,(4), 515-521, Coden:HCACAV;ISSN: 0018-019X, 1999, XP002372297.
Patent Abstracts of Japan vol. 008, No. 018(p. 250), Jan. 26, 1984 (JPO abstract which corresponds to JP 58176538 A (Sharp KK), Oct. 17, 1983 which was previously sent with EPO abstract).
U.S. Appl. No. 10/128,804, filed Aug. 2005, Cruse.
U.S. Appl. No. 11/398,125, filed Apr. 2006, Cruse.
U.S. Appl. No. 11/398,132, filed Apr. 2006, Cruse.
U.S. Appl. No. 10/922,426, filed Aug. 2004, Cruse et al.
U.S. Appl. No. 11/208,367, filed Aug. 2005, Cruse et al.
U.S. Appl. No. 10/903,960, filed Jul. 2004, Weller.
The Siloxane Bond, Physical Properties and Chemical Transformations, M.G. Voronkov, V.P. Mileshkevich and Yu A. Yuzhelevskii, Consultant Bureau, A Division of Plenum Publishing Company, New York (1978), Chapter 5.

(Continued)

*Primary Examiner*—Robert D. Harlan
(74) *Attorney, Agent, or Firm*—Dominick G. Vicari

(57) ABSTRACT

Silane compositions of the general formula are provided herein comprising

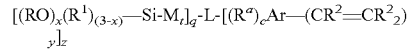

wherein R and $R^1$ are independently a hydrocarbon group of from 1 to about 20 carbon atoms; $R^2$ are each independently hydrogen or a hydrocarbon group of from 1 to about 20 carbon atoms; M optionally is a divalent hydrocarbon connecting group of from 1 to about 20 carbon atoms to link the silicon atom and the L group; L is a covalently bound hydrocarbon linking group of from 1 to about 20 carbon atoms or a heteroatom linking group selected from the group consisting of —O—, —S—, —$NR^3$— wherein $R^3$ is hydrogen or a hydrocarbon group of from 1 to about 20 carbon atoms; $R^a$ is an alkyl group of 1 to 12 carbon atoms; Ar is a substituted or unsubstituted aromatic group; q is an integer of 1 to 4; t and c are each independently 0 or 1; and x, y and z are each independently integers of 1 to 3, inclusive, with the proviso that t is 1 when L is a heteroatom group. Also provided are processes for preparing the silane compositions and rubber composition comprising the silane compositions.

63 Claims, No Drawings

U.S. PATENT DOCUMENTS

| | | |
|---|---|---|
| 6,242,627 B1 | 6/2001 | Gedon et al. |
| 6,359,046 B1 | 3/2002 | Cruse |
| 6,414,061 B1 | 7/2002 | Cruse |
| 6,416,817 B1 * | 7/2002 | Rangwalla et al. .......... 427/377 |
| 6,465,581 B1 | 10/2002 | Wideman et al. |
| 6,528,673 B2 | 3/2003 | Cruse |
| 6,548,594 B2 | 4/2003 | Luginsland |
| 6,608,125 B2 | 8/2003 | Cruse |
| 6,635,700 B2 | 10/2003 | Cruse et al. |
| 6,683,135 B2 | 1/2004 | Cruse |
| 6,777,569 B1 | 8/2004 | Westmeyer |
| 6,849,754 B2 | 2/2005 | Deschler et al. |
| 7,019,074 B2 * | 3/2006 | Nakamura et al. ............ 525/63 |
| 7,074,876 B2 | 7/2006 | Cruse |
| 7,078,551 B2 | 7/2006 | Cruse |
| 7,081,500 B2 | 7/2006 | Cruse |
| 7,122,590 B2 | 10/2006 | Cruse |
| 2001/0009966 A1 | 7/2001 | Wunsch |
| 2002/0016487 A1 | 2/2002 | Kayser et al. |
| 2003/0130388 A1 | 7/2003 | Luginsland |
| 2003/0181562 A1 | 9/2003 | Belin et al. |
| 2003/0199619 A1 | 10/2003 | Cruse |
| 2004/0014840 A1 | 1/2004 | Hong et al. |
| 2005/0009955 A1 | 1/2005 | Cohen et al. |
| 2005/0245753 A1 | 11/2005 | Cruse |
| 2005/0245754 A1 | 11/2005 | Glatzer |
| 2006/0025506 A1 | 2/2006 | Weller |
| 2006/0041063 A1 | 2/2006 | Cruse |
| 2006/0183831 A1 | 8/2006 | Hsu et al. |
| 2007/0197725 A1 | 8/2007 | Chaves |
| 2007/0197812 A1 | 8/2007 | Chaves |
| 2007/0197813 A1 | 8/2007 | Chaves |
| 2007/0228322 A1 | 10/2007 | Chaves |

FOREIGN PATENT DOCUMENTS

| | | |
|---|---|---|
| DE | 2050467 | 5/1971 |
| DE | 10163945 | 5/2003 |
| EP | 0 097 516 | 1/1984 |
| EP | 0097516 | 1/1984 |
| EP | 0 396 364 | 11/1990 |
| EP | 0631982 | 1/1995 |
| EP | 0784072 | 7/1997 |
| EP | 784072 | 7/1997 |
| EP | 02/22728 A1 | 3/2001 |
| EP | 01/49783 A1 | 7/2001 |
| EP | 01/96442 A1 | 12/2001 |
| FR | 2 382 456 | 9/1978 |
| JP | 581 76 538 | 10/1983 |
| JP | 58176538 | 10/1983 |
| JP | 07258474 | 10/1995 |
| JP | WO2004/005395 | 1/2004 |
| WO | WO99/09036 | 2/1999 |
| WO | WO99/20682 | 4/1999 |
| WO | WO 99/20682 | 4/1999 |
| WO | 01/49781 A1 | 7/2001 |
| WO | 01/49782 A1 | 7/2001 |
| WO | 03/091314 | 11/2003 |
| WO | WO2005/007660 | 1/2005 |
| WO | WO2005/040272 | 5/2005 |
| WO | WO2006/019963 | 2/2006 |

OTHER PUBLICATIONS

Joshi PG: Low Voc Silanes for Silica Tires:; Spring Technical Meeting-American Chemical Society, Rubber Division, 167th San Antonio, Texas USA, May 16, 2005-May 18, 2005, pp. 47/1-47/9, XP009072692, ISSN: 1547-1969.

Teng, Zhu et al.; "Palladium-induced intramolecular coupling reactions of some alkenyl (2-iodobenzyl)silanes" Helvetica Chimica Acta, 82,(4), 515-521, Conden;HCACAV;ISSN: 0018-019X, 1999, XP002372297.

GE Advanced Materials Silicones "Low VOC Silanes for Silica Tire", Feb. 22, 2005.

Bonsignore P.V. et al., (1960) APolyalkylene disulfides and polysulfides containing silicon@, *Journal of Organic Chemstry* 25 pp. 237-240.

Takiguchi T. et al. (1983) Some Fundamental Investigations Viewed in Industrial Aspects on the Synthesis of Organosilicon Monomers and Polymers with Some Novel Properties and Functions@, *AGKGAA* 43 pp. 75-82.

Dvorak, M. et al. (1977) ACarbonfunctional organosilicon compounds substituted in the alpha-position. II. Phosphorus-containing organosilicon compounds substituted in the .alpha.-position. II. Phosphorus-containing organosilicon compounds@. *Chemicky Prumysl*, 27(5), pp. 9-2789.

Andrianov, K.A. et al. (1962) AReaction of replacement of chlorine in .alpha.-chloromethylalkoxysilanes by residues of diethyl or dibutyl dithiophosphoric or diphenyldithiophosphinic acids@. *Izvestiya Akademii Nauk SSSR*, pp. 2-3353.

Prashant G. Joshi, GE Advanced Materials—Silicones, "Low Voc Silanes for Silica Tires", 2005.

Teng et al., Palladium-Induced Intramolecular Coupling Reactions of Some Alkenyl(*o*-iodobenzyl) silanes, *Helvetica Chimica Acta*, vol. 82, pp. 515-521(1999) XP-0023372297.

* cited by examiner

SILANE COMPOSITIONS, PROCESSES FOR THEIR PREPARATION AND RUBBER COMPOSITIONS CONTAINING SAME

CROSS-REFERENCE TO RELATED APPLICATIONS

The instant application is a Continuation-In-Part application of U.S. Ser. No. 10/903,960 filed Jul. 30, 2004.

BACKGROUND OF THE INVENTION

1. Technical Field

The present invention relates generally to silane compositions, processes for their preparation and rubber compositions containing same.

2. Description of the Related Art

The tire treads of modern tires must meet performance standards which require a broad range of desirable properties. Generally, three types of performance standards are important in tread compounds. They include good wear resistance, good traction and low rolling resistance. Major tire manufacturers have developed tire tread compounds which provide lower rolling resistance for improved fuel economy and better skid/traction for a safer ride. Thus, rubber compositions suitable for, e.g., tire treads, should exhibit not only desirable strength and elongation, particularly at high temperatures, but also good cracking resistance, good abrasion resistance, desirable skid resistance and low tangent delta values at low frequencies for desirable rolling resistance of the resulting treads. Additionally, a high complex dynamic modulus is necessary for maneuverability and steering control.

Presently, silica has been added to rubber compositions as a filler to replace some or substantially all of the carbon black filler to improve these properties, e.g., lower rolling resistance. Although more costly than carbon black, the advantages of silica include, for example, improved wet traction, low rolling resistance, etc., with reduced fuel consumption. However, as compared to carbon black, there tends to be a lack of, or at least an insufficient degree of, physical and/or chemical bonding between the silica particles and the rubber to enable the silica to become a reinforcing filler for the rubber thereby giving less strength to the rubber. Therefore, a silica filler system typically requires the use of coupling agents.

Generally, coupling agents are used to enhance the rubber reinforcement characteristics of silica. Such coupling agents, for example, may be premixed or pre-reacted with the silica particles or added to the rubber mix during the rubber/silica processing, or mixing, stage. If the coupling agent and silica are added separately to the rubber mix during the rubber/silica processing, or mixing, stage, it is considered that the coupling agent then combines in situ with the silica.

A coupling agent is typically a bi-functional molecule that will react with the silica at one end thereof and cross-link with the rubber at the other end. In this manner, the reinforcement and strength of the rubber, e.g., the toughness, strength, modulus, tensile and abrasion resistance, are particularly improved. The coupling agent is believed to cover the surface of the silica particle which then hinders the silica from agglomerating with other silica particles. By interfering with the agglomeration process, the dispersion is improved and therefore the wear and fuel consumption are also improved. Present coupling agents have several problems associated with them such as, for example, toxicity and compatibility problems with other ingredients employed in the rubber composition.

Accordingly, there exists a need for improved coupling agents.

BRIEF DESCRIPTION OF THE INVENTION

In accordance with one embodiment of the present invention, a silane composition is provided comprising

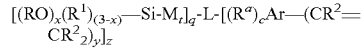

wherein R and $R^1$ are independently a hydrocarbon group of from 1 to about 20 carbon atoms; $R^2$ are each independently hydrogen or a hydrocarbon group of from 1 to about 20 carbon atoms; $R^a$ is an alkylene group of 1 to 12 carbon atoms, M is a divalent hydrocarbon connecting group of from 1 to about 20 carbon atoms to link the silicon atom and the L group; L is a covalently bound hydrocarbon linking group of from 1 to about 20 carbon atoms or a heteroatom linking group selected from the group consisting of —O—, —S—, —$NR^3$— wherein $R^3$ is a bond or a hydrocarbon group of from 1 to about 20 carbon atoms; Ar is a substituted or unsubstituted aromatic group; q is an integer of 1 to 4; t and c are each independently 0 or 1; and x, y and z are each independently integers of 1 to 3, inclusive, with the proviso that t is 1 when L is a heteroatom group.

In accordance with a second embodiment of the present invention, a process for the preparation of a silane composition is provided comprising reacting at least one silane reactant represented by the general formula

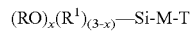

wherein R, $R^1$, M and x have the aforestated meanings and T is a compound selected from the group consisting of a mercapto compound, a hydroxy compound and an amine of the general formula —$NR^4R^5$ wherein $R^4$ and $R^5$ are independently hydrogen or a hydrocarbon group of from 1 to about 20 carbon atoms and wherein at least one of $R^4$ and $R^5$ is hydrogen, with at least one unsaturated reactant represented by the general formula $$X—(R^a)_c Ar—(CR^2=CR^2_2)_y$$

wherein Ar, $R^2$, $R^a$, c and y have the aforestated meanings and X is an anion of an organic or inorganic acid; in the presence of an effective amount of at least one base.

In accordance with a third embodiment of the present invention, a process for the preparation of a silane composition is provided comprising reacting at least one silicon hydride represented by the general formula $R_b HSiZ_{3-b}$ wherein each R is independently a hydrocarbon group of from 1 to about 20 carbon atoms; Z is a halogen atom, and b is from 0 to 3, with at least one unsaturated reactant represented by the general formula

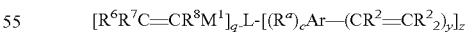

wherein Ar, $R^2$, L, $R^a$, c, q, y and z have the aforestated meanings, $R^6$, $R^7$ and $R^8$ are each independently hydrogen or a hydrocarbon group of from 1 to about 6 carbon atoms, $M^1$ is a bond or divalent hydrocarbon connecting group from 1 to about 18 carbon atoms wherein $R^6$, $R^7$, $R^8$, and $M^1$ have a combined total of carbon atoms of no more than about 18, in the presence of at least one hydrosilating catalyst.

In accordance with a fourth embodiment of the present invention, a rubber composition is provided comprising (a) a rubber component; (b) a filler; and (c) at least one silane composition of the general formula

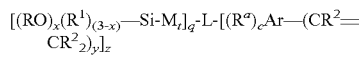

wherein R, $R^1$, $R^2$, $R^a$, M, L, Ar, x, t, c, q, y and z have the aforestated meanings and with the proviso that t is 1 when L is a heteroatom group.

In accordance with a fifth embodiment of the present invention, a process for preparing a rubber composition is provided comprising adding to a rubber composition reaction forming mixture an effective amount of at least one silane composition of the general formula

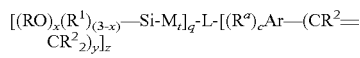

wherein R, $R^1$, $R^2$, $R^a$, M, L, Ar, x, t, c, q, y and z have the aforestated meanings and with the proviso that t is 1 when L is a heteroatom group.

The term "phr" is used herein as its art-recognized sense, i.e., as referring to parts of a respective material per one hundred (100) parts by weight of rubber.

DETAILED DESCRIPTION OF THE INVENTION

In one embodiment of the present invention, silane compositions of the general formula are provided:

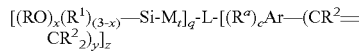

wherein R and $R^1$ are independently a hydrocarbon group of from 1 to about 20 carbon atoms including, by way of illustration, straight or branched aliphatic, cycloaliphatic and aromatic groups and cycloaliphatic and aromatic groups substituted with one or more straight or branched aliphatic, cycloaliphatic and/or aromatic groups; $R^2$ are each independently hydrogen or a hydrocarbon group of from 1 to about 20 carbon atoms in one embodiment or 1 to 6 carbon atoms in a second embodiment including, by way of illustration, alkyl radicals, substituted alkyl radicals, cycloaliphatic or aromatic groups; M is a divalent hydrocarbon connecting group of from 1 to about 20 carbon atoms in one embodiment or a divalent alkyl connecting group of 1 to 8 carbon atoms in a second embodiment to link the silicon atom and the L group; L is a covalently bound hydrocarbon linking group of from 1 to about 20 carbon atoms or a heteroatom linking group selected from the group consisting of —O—, —S—, —$NR^3$— wherein $R^3$ is a bond or a hydrocarbon group of from 1 to about 20 carbon atoms; $R^a$ is an alkylene group of from 1 to 12 carbon atoms; Ar is a saturated or unsaturated aromatic group (e.g., benzene or benzyl) optionally substituted with one or more straight or branched aliphatic, cycloaliphatic and/or aromatic groups of 1 to 12 carbon atoms; q is an integer of 1 to 4; t and c are each independently 0 or 1; and x, y and z are each independently integers of 1 to 3, inclusive with the proviso that t is 1 when L is a heteroatom group. In one embodiment, L can be any multi-functional aromatic group, or cyclic or linear aliphatic hydrocarbon groups of 1 to about 20 carbon atoms. In one embodiment, each R is independently an alkyl radical of 1 to 8 carbon atoms. In a second embodiment, each R is independently an alkyl radical of 1 to 3 carbon atoms. In a third embodiment, each R is independently an alkyl radical of 2 carbon atoms. In one embodiment, each $R^1$ is independently an alkyl radical of 1 to 6 carbon atoms. In a second embodiment, each $R^1$ is independently an alkyl radical of 1 to 3 carbon atoms. In a third embodiment, each $R^1$ is independently an alkyl radical of 1 carbon atom.

Generally, the foregoing silane compositions of this invention can be obtained by reacting at least one silane reactant represented by the general formula

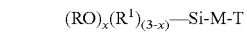

wherein R, $R^1$, M and x have the aforestated meanings and T is one or more compounds selected from the group consisting of a mercapto compound, a hydroxy compound and an amine of the general formula —$NR^4R^5$ wherein $R^4$ and $R^5$ are independently hydrogen or a hydrocarbon group of from 1 to about 20 carbon atoms and wherein at least one of $R^4$ and $R^5$ are hydrogen, with at least one unsaturated reactant represented by the general formula

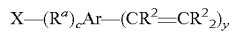

wherein Ar, $R^2$, $R^a$, c and y have the aforestated meanings and X is an anion of an organic or inorganic acid; in the presence of an effective amount of at least one base. Useful anions of an organic or inorganic acid include, for example, a halogen atom (i.e., F, Cl, Br, or I), sulfonate group, sulfinate group or carboxylate group and the like and combinations thereof. From a synthetic chemical standpoint, X is any group which can function as a leaving group during nucleophilic substitution reactions. Suitable halides for use herein include, for example, chloro, bromo, fluoro, etc., and the like.

Examples of the silane reactants include aminosilanes such as 3-aminopropyltrimethoxysilane, 3-aminopropyldimethylmethoxysilane, 3-aminopropylmethyldimethoxysilane, 3-(aminopropyl)ethyldimethoxysilane, 3-aminopropyltriethoxysilane, 3-aminopropyldimethylethoxysilane, 3-aminopropylphenyldimethoxysilane, 2-aminoethyltriethoxysilane, 4-aminobutyltriethoxysilane, 4-aminobutyltrimethoxysilane, 4-aminobutylmethyldimethoxysilane, 4-(trimethoxysilyl)-2-butanamine, 3-[diethoxy(hexyloxy)silyl]-1-propanamine, 3-[tris(pentyloxy)silyl]-1-propanamine, 3-[tris(2,2,2-trifluoroethoxy)silyl]-1-propanamine, 3-[tris[2-(2-phenoxyethoxy)ethoxy]silyl]-1-propanamine, 3-[tris[(2-ethylhexyl)oxy]silyl]-1-propanamine, 3-[tris(hexyloxy)silyl]-1-propanamine, 3-triisopropoxysilylpropylamine, 3-[tris(3-methylbutoxy)silyl]-1-propanamine, 3-[tris(2-ethoxyethoxy)silyl]-1-propanamine, 3-[bis(1,1-dimethylethoxy)methoxysilyl]-1-propanamine, 3-[(1,1-dimethylethoxy)diethoxysilyl]-1-propanamine, 3-[(1,1-dimethylethoxy)dimethoxysilyl]-1-propanamine, 3-(trimethoxysilyl)-1-pentanamine, 4-amino-3,3-dimethylbutyltrimethoxysilane, 4-amino-3,3-dimethylbutyltriethoxysilane, and the like; mercaptosilanes such as mercaptopropyltriethoxysilane and the like. The silane reactants can be made by any commercially available method, e.g., the aminosilanes can be prepared by the processes disclosed in U.S. Pat. No. 6,242,627. In one embodiment, the unsaturated reactants include vinylbenzylchloride and/or divinylbenzylchloride. In another embodiment, the unsaturated reactant is vinylbenzylchloride.

The reaction of the at least one silane reactant and at least one unsaturated reactant is advantageously carried out in the presence of an effective amount of at least one base. The base(s) employed herein can be any strong base. Suitable strong bases include, but are not limited to, an alkoxides (alcoholate) of an alkali metal, alkoxides (alcoholate) of an alkaline earth metal and the like and mixtures thereof. Examples of useful alkoxides include sodium methoxide, sodium ethoxide, calcium methoxide, calcium ethoxide, sodium propoxide, sodium tert-butoxide, potassium propoxide, potassium tert-butoxide, lithium methoxide, lithium ethoxide, lithium propoxide, lithium tert-butoxide and the like and combinations thereof. Alternatively, the bases for use herein can be amines, amides and the like and combinations thereof. Examples of such amines and amides include tertiary amines, heterocyclic tertiary organic amines and N,N-di-substituted amides, e.g., triphenylamine, tribenzylamine, trimethylamine, triethylamine, tripropylamine, tributylamine, triisobutylamine, trioctylamine, pyridine, quinoline, N,N-dimethylaniline, N-methyl-2-pyrrolidone and polyvinyl pyrrolidone and combinations thereof. In one embodiment the amine catalysts for use herein are the tertiary amines, for example, trialkylmonoamines such as triethylamine, tributylamine, diisopropylethylamine, etc.; and trialkyldiamines such as diazabicyclooctane, diazabicycloundecane, tetramethylethyldiamine, etc. In another embodiment, triethylamine and diisopropylethylamine are used as the amine catalyst.

As one skilled in the art would readily appreciate, the foregoing reaction to form the silane compositions of this invention can be carried out by first mixing the at least one base with the silane reactant to form a mixture and then combining the mixture with the unsaturated reactant. Alternatively, the reaction can be carried out by adding the base to the reaction medium of the silane and unsaturated reactants in a simple operation step or in multiple stages. In general, the effective amount of the base employed in the process of this invention can ordinarily range from about 1 molar equivalent to about 10 molar equivalents to the silane reactant and all subranges therebetween. In another embodiment, the effective amount of the base employed in the process of this invention can range from about 1.1 molar equivalent to about 2 molar equivalents to the silane reactant and all subranges therebetween.

The at least one silane reactant and at least one unsaturated reactant are advantageously reacted in a desired ratio to form the silane compositions of the present invention. The reaction may be carried out at a temperature ranging from about 0° C. to about 120° C. and all subranges therebetween. In another embodiment, the temperature for the reaction may range from about 25° C. to about 70° C. and all subranges therebetween. The time period for the reaction may range from about 1 hour to about 24 hours and all subranges therebetween. Generally, the molar ratio of silane reactant to unsaturated reactant will range from about 1:0.1 to about 1:10 and all subranges therebetween. In another embodiment, the molar ratio of silane reactant to unsaturated reactant will range from about 1:0.5 to about 1:2 and all subranges therebetween.

It will be understood by those skilled in the art that the foregoing silane composition may be a reaction product containing a complex mixture of compounds, e.g., in the case where T of the silane reactant is an amine of the formula —NH$_2$. The reaction product mixture thus obtained need not be separated to isolate one or more specific components. Thus, the reaction product mixture can be employed as is in a rubber composition of this invention. Accordingly, upon completion of the reaction, the solution of the reaction product of the silane and unsaturated reactants, the base, and any byproduct alcohol, can be additionally filtered and/or stripped using any known commercially available techniques, e.g., vacuum or pressure filtration, to remove any unwanted base, byproducts or volatile heavies.

In another process of the present invention, the foregoing silane compositions can be obtained by reacting at least one silicon hydride with at least one unsaturated reactant represented by the general formula

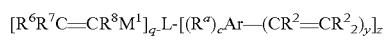

wherein Ar, $R^2$, L, $R^a$, c, q, y and z have the aforestated meanings, $R^6$, $R^7$ and $R^8$ are each independently hydrogen or a hydrocarbon group of from 1 to about 6 carbon atoms, e.g., alkyl groups having one to about 6 carbon atoms, cycloalkyls having four to about 6 carbon atoms (e.g., cyclopentane, cyclohexane), and aryls (e.g., phenyl), $M^1$ is a bond or divalent hydrocarbon connecting group from 1 to about 18 carbon atoms wherein $R^6$, $R^7$, $R^8$, and $M^1$ have a combined total of carbon atoms of no more than about 18, in the presence of at least one hydrosilating catalyst.

Suitable silicon hydrides useful in this process are described by the formula $R_b HSiZ_{3-b}$ wherein each $R_b$ is independently a hydrocarbon group of from 1 to about 20 carbon atoms including, by way of example, alkyl groups having one to about 20 carbon atoms, cycloalkyls having about four to about 12 carbon atoms, and aryls; b is from 0 to 3 and Z is a halogen atom (e.g., F, Cl, Br, or I): Examples of silicon hydrides described by the formula above which may be useful in this process include trimethylsilane, dimethylsilane, triethylsilane, dichlorosilane, trichlorosilane, methyldichlorosilane, dimethylchlorosilane, ethyldichlorosilane, cyclopentyldichlorosilane, methylphenylchlorosilane, (3,3,3-trifluoropropyl) dichlorosilane and the like and mixtures thereof. In one embodiment, the silicon hydrides include at least one of dimethylchlorosilane, methyldichlorosilane, dichlorosilane and trichlorosilane. In another embodiment of the present invention, the silicon hydride is trichlorosilane. Examples of suitable unsaturated reactants for use in this process include diethylenebenzene, diisopropenylbenzene, dibutylenebenzene, 1,4-bis(2-methylstyryl)-benzene and the like and mixtures thereof.

The silicon hydride and unsaturated reactant are typically contacted in the presence of a hydrosilating catalyst to form a hydrosilated compound. Any hydrosilating catalyst can be used herein, e.g., a catalyst containing at least an active hydrosilating metal in elemental or compound form. Useful active hydrosilating metal catalysts include, but are not limited to, ruthenium, rhodium, cobalt, palladium, iridium, platinum, chromium and molybdenum metals in elemental or compound form. In one embodiment, the active hydrosilating metal is ruthenium or platinum in elemental or compound form.

An illustrative list of the hydrosilating metal catalysts which may be employed in this embodiment include, by way of example, group VIII compounds such as $RhCl_3$, $Rh(PPh_3)_3Cl$ (where Ph is a phenyl group), $H_2PtCl_6$, soluble platinum catalysts including Speier's catalyst ($H_2 PtCl_6$ in i-PrOH), Karstedt's catalyst (the reaction product of $H_2PtCl_6$ and divinyltetramethyldisiloxane as described in U.S. Pat. Nos. 3,715,334 and 3,775,452), Ashby's catalyst (the reaction product of $H_2PtCl_6$ and tetravinyltetramethyldisiloxane as described in U.S. Pat. Nos. 3,159,601 and 3,159,662) and Lamoreoux's catalyst ($H_2 PtCl_6$ in n-octanol as described in U.S. Pat. No. 3,220,972).

In another embodiment, the hydrosilating catalyst can be one or more active free-radical initiators. Any active free-radical initiator can be used herein. Examples of such active free-radical initiators include, but are not limited to, organic peroxide-type initiators, e.g., acetyl-peroxide, t-butyl-peroxide, benzoyl-peroxide and the like; azo-type initiators, e.g., azo-bis-isobutyronitrile, and the like and mixtures thereof.

When silating the unsaturated reactants in this invention, any reaction vessel conventional in the art may be employed. The reaction vessel may be charged with the system comprising at least the one silicon hydride reactant, unsaturated reactant, and hydrosilating metal catalyst, with the particular order of addition not being limited. Stirring may be employed but is not required in order to enhance the reaction. In one embodiment, the hydrosilation reaction may be conducted at ambient temperature to about 160° C. and all subranges therebetween. In a second embodiment, the hydrosilation reaction may be conducted at a temperature from about 40° C. to about 100°C. and all subranges therebetween. Additionally, the reaction may occur at atmospheric pressure; however, the pressure may be increased if desired, and substantially inert organic solvents like toluene may also be used to enhance the reaction conditions.

The amount of the silicon hydride reactant, unsaturated reactant, and hydrosilating catalyst employed in the process of this invention is not limited. The only requirement is that the desired hydrosilation reactions occur. In one embodiment, the hydrosilating catalyst can advantageously be used at concentrations of about 0.1 ppm to about 1 part. In a second embodiment, the hydrosilating catalyst can be used at a concentration of about 10 ppm to about 1000 ppm. The molar ratio of silicon hydride reactant to unsaturated reactant can vary widely, e.g., from about 1:100 to about 100:1. In another embodiment, the molar ratio of silicon hydride to unsaturated reactant can range from about 1:10 to about 10:1. In yet another embodiment, the molar ratio of silicon hyride to unsaturated reactant can range from about 2:1 to about 1:2.

If necessary, following the hydrosilation reaction the hydrosilated composition can be further reacted, for example, to provide alkoxy groups on the silicon atom. For example, in the case where a halogen atom is attached to the silicon, e.g., when trichlorosilane is employed as the silicon hydride, the hydrosilated composition of the present invention can be prepared by reacting the foregoing hydrosilated composition with an effective amount of one or more ether-forming agents under ether forming reaction conditions. Useful ether-forming agents include, but are not limited to, alkylorthoformate, dialkylorthoformate, trialkylorthoformate, e.g., triethylorthoformate, and the like and mixtures thereof. In one embodiment, the alkoxy groups can be advantageously bonded to the silicon atom at a temperature of from about 0° C. to about 100° C. and all subranges therebetween. In a second embodiment, the alkoxy groups can be advantageously bonded to the silicon atom at a temperature of from about 25° C. to about 80° C. and all subranges therebetween. The reaction can be carried out in the absence of a catalyst, or in the presence of a catalyst, for example, acid-type mineral acid catalysts such as sulfonic acids, Lewis type acids and the like and mixtures thereof. In one embodiment, concentration of the ether-forming agent will ordinarily range from about 0.5 molar equivalents to about 100 molar equivalents to the residual halogen atoms of the hydrosilated compound and all subranges therebetween. In a second embodiment, concentration of the ether-forming agent will ordinarily range from about 1 molar equivalents to about 10 molar equivalents to the residual halogen atoms of the hydrosilated compound and all subranges therebetween.

As one skilled in the art will readily appreciate, depending on the particular reaction and reaction conditions not all of the desired alkoxy groups may form, e.g., in the case of further reacting the reaction product obtained from the reaction of trichlorosilane with the unsaturated reactant, the alkoxylated hydrosilated composition may not be fully alkoxylated and may still have one chloride group attached to the silicon atom. Accordingly, in order to provide a trialkoxysilane composition, it may be necessary to be further react the alkoxylated hydrosilated intermediate to remove the remaining chloride group, e.g., by further reacting the alkoxylated hydrosilated intermediate with a second ether-forming agent under ether-forming reaction conditions. In one embodiment, the reaction can be carried out at a temperature of from about 0° C. to about 80° C. and all subranges therebetween. In a second embodiment, the reaction can be carried out at a temperature from about 20° C. to about 75° C. and all subranges therebetween. Useful ether-forming agents include, but are not limited to, alcohol, e.g., methanol, ethanol, etc., and the like. The reaction can be carried out in the absence of a base, or in the presence of a base, e.g., trialkylamines such as triethylamine. In one embodiment, concentration of the second ether-forming agent will ordinarily range from about 0.5 molar equivalents to about 100 molar equivalents to the alkoxylated hydrosilated intermediate and all subranges therebetween. In a second embodiment, concentration of the second ether-forming agent will ordinarily range from about 1 molar equivalents to about 20 molar equivalents to the alkoxylated hydrosilated intermediate and all subranges therebetween. Upon completion of the reaction, the solution can be additionally filtered and/or stripped using any known commercially available techniques, e.g., vacuum or pressure filtration, to remove any unwanted catalyst, byproducts or volatile heavies.

The silane compositions of this invention are useful as coupling agents. In one embodiment, the silane compositions of this invention are particularly useful as a coupling agent in rubber compositions. Generally, the rubber compositions of the present invention will contain at least (a) a rubber component; (b) a filler; and (c) at least one of the foregoing silane compositions.

The rubber components for use in the rubber compositions of the present invention are based on unsaturated rubbers such as, for example, natural or synthetic rubbers. Representative of the highly unsaturated polymers that can be employed in the practice of this invention are diene rubbers. Such rubbers will ordinarily possess an iodine number of between about 20 to about 400 and all subranges therebetween, although highly unsaturated rubbers having a higher or a lower (e.g., of about 50 to about 100 and all subranges therebetween) iodine number can also be employed. Illustrative of the diene rubbers that can be utilized are polymers based on conjugated dienes such as, for example, 1,3-butadiene; 2-methyl-1,3-butadiene; 1,3-pentadiene; 2,3-dimethyl-1,3-butadiene; and the like, as well as copolymers of such conjugated dienes with monomers such as, for example, styrene, alpha-methylstyrene, acetylene, e.g., vinyl acetylene, acrylonitrile, methacrylonitrile, methyl acrylate, ethyl acrylate, methyl methacrylate, ethyl methacrylate, vinyl acetate, and the like. In one embodiment, highly unsaturated rubbers are employed and include, but are not limited to, natural rubber, cis-polyisoprene, polybutadiene, poly(styrene-butadiene), styrene-isoprene copolymers, isoprene-butadiene copolymers, styrene-isoprene-butadiene tripolymers, polychloroprene, chloro-isobutene-isoprene, nitrile-chloroprene, styrene-chloroprene, and poly(acrylonitrile-butadiene). Moreover, mixtures of two or more highly unsaturated rubbers with elastomers having lesser unsaturation such as EPDM, EPR, butyl or halogenated butyl rubbers are also within the contemplation of the invention.

Fillers for use in the rubber composition of the present invention include, but are not limited to, metal oxides, such as silica (e.g., pyrogenic and precipitated), titanium dioxide, aluminosilicate and alumina, siliceous materials including clays and talc, and carbon black and the like and mixtures thereof. The term "alumina" can be described herein as aluminum oxide, or $Al_2O_3$. The fillers may be hydrated or in anhydrous form.

Silica fillers may be of any type that is known to be useful in connection with the reinforcing of rubber compositions. Examples of suitable silica fillers include, but are not limited to, silica, precipitated silica, amorphous silica, vitreous silica, fumed silica, fused silica, synthetic silicates such as aluminum silicates, alkaline earth metal silicates such as magnesium silicate and calcium silicate, natural silicates such as kaolin and other naturally occurring silicas and the like. Also useful are highly dispersed silicas having, e.g., in one embodiment BET surfaces of from about 5 to about 1000 $m^2/g$ and all subranges therebetween and in a second embodiment from about 20 to about 400 $m^2/g$ and all subranges therebetween and primary particle diameters of from about 5 to about 500 nm and all subranges therebetween and also from about 10 to about 400 nm and all subranges therebetween. These highly dispersed silicas can be prepared by, for example, precipitation of solutions of silicates or by flame hydrolysis of silicon halides. The silicas can also be present in the form of mixed oxides with other metal oxides such as, for example, Al, Mg, Ca, Ba, Zn, Zr, Ti oxides and the like. Commercially available silica fillers known to one skilled in the art include, e.g., those available from such sources as Cabot Corporation under the Cab-O-Sil® tradename; PPG Industries under the Hi-Sil and Ceptane tradenames; Rhodia under the Zeosil tradename and Degussa AG under the Ultrasil and Coupsil tradenames. Mixtures of two or more silica fillers can be used in preparing the rubber composition of this invention.

The silica filler is incorporated into the rubber composition in amounts that can vary widely. In one embodiment, the amount of silica filler can range from about 5 to about 100 phr and all subranges therebetween. In a second embodiment, the amount of silica filler can range from about 25 to about 85 phr and all subranges therebetween.

Suitable carbon black fillers include any of the commonly available, commercially-produced carbon blacks known to one skilled in the art, e.g., in one embodiment the carbon blacks can be those having a surface area (EMSA) of at least 20 $m^2/g$ and in a second embodiment the carbon blacks can be those having an EMSA of at least 35 $m^2/g$ up to 200 $m^2/g$ or higher. Surface area values used in this application are those determined by ASTM test D-3765 using the cetyltrimethylammonium bromide (CTAB) technique. Among the useful carbon blacks are furnace black, channel blacks and lamp blacks. More specifically, examples of the carbon blacks include super abrasion furnace (SAF) blacks, high abrasion furnace (HAF) blacks, fast extrusion furnace (FEF) blacks, fine furnace (FF) blacks, intermediate super abrasion furnace (ISAF) blacks, semi-reinforcing furnace (SRF) blacks, medium processing channel blacks, hard processing channel blacks and conducting channel blacks. Other carbon blacks which may be utilized include acetylene blacks. Mixtures of two or more of the above blacks can be used in preparing the rubber compositions of the invention. Typical values for surface areas of usable carbon blacks are summarized in the following Table 1.

TABLE 1

Carbon Blacks

| ASTM Designation (D-1765-82a) | Surface Area ($m^2/g$) (D-3765) |
|---|---|
| N-110 | 126 |
| N-234 | 120 |
| N-220 | 111 |
| N-339 | 95 |
| N-330 | 83 |
| N-550 | 42 |
| N-660 | 35 |

The carbon blacks utilized in the invention may be in pelletized form or an unpelletized flocculent mass. In one embodiment, pelletized carbon black is employed for ease of handling. In one embodiment, the carbon blacks can be incorporated into the rubber compositions in amounts ranging from about 0.5 to about 100 phr and all subranges therebetween. In a second embodiment, the carbon blacks can be incorporated into the rubber compositions in amounts ranging from about 1 to about 85 phr and all subranges therebetween.

The silane compositions of this invention may be premixed, or prereacted, with the filler particles or added to the rubber mix during the rubber and filler processing, or mixing stage. If the silane composition and filler are added separately to the rubber mix during the rubber and filler mixing, or processing stage, it is considered that the silane composition then combines in situ with the filler. In one embodiment, the silane composition will be present in the rubber compositions in an amount ranging from about 0.05 to about 25 phr and all subranges therebetween. In a second embodiment, the silane composition will be present in the rubber compositions in an amount ranging from about 1 to about 10 phr and all subranges therebetween.

The rubber compositions of this invention can be formulated in any conventional manner known in the rubber compounding art with various commonly used additive materials. Examples of such commonly used additive materials include curing aids, e.g., sulfur; activators; retarders; accelerators; processing additives, e.g., oils; resins, e.g., tackifying resins; plasticizers; pigments; fatty acids; zinc oxide; waxes; antioxidants; antiozonants; peptizing agents; reinforcing materials and the like and combinations thereof. Depending on the intended use of the rubber composition, the additives mentioned above are selected and commonly used in conventional amounts.

Generally, accelerators are used to control the time and/or temperature required for vulcanization and to improve the properties of the vulcanizate. In one embodiment, a single accelerator system may be used, i.e., a primary accelerator. In one embodiment, a primary accelerator(s) may be used in total amounts ranging from about 0.5 to about 4 phr and all subranges therebetween. In a second embodiment, a primary accelerator(s) may be used in total amounts ranging from about 0.8 to about 1.5 phr and all subranges therebetween. Combinations of a primary and a secondary accelerator can also be used with the secondary accelerator being employed in smaller amounts (of about 0.05 to about 3 phr and all subranges therebetween) in order to activate and to improve the properties of the vulcanizate. Delayed action accelerators may also be used. Vulcanization retarders may also be used. Suitable types of accelerators are, for example, amines, disulfides, guanidines, thioureas, thiazoles, thiurams, sulfenamides, dithiocarbamates, and xanthates. In one embodiment, the primary accelerator is a sulfenamide. If a second accelerator is used, the secondary accelerator may be a guanidine, dithiocarbamate, or thiuram compound.

In one embodiment, amounts of tackifier resins can range from about 0.5 to about 10 phr and all subranges therebetween. In a second embodiment, amounts of tackifier resins can range from about 1 to about 5 phr and all subranges therebetween. Amounts of processing aids can range from about 1 to about 50 phr and all subranges therebetween. Such processing aids include, for example, aromatic, naphthenic, and/or paraffinic processing oils. Amounts of antioxidants can range from about 1 to about 5 phr. Such antioxidants include, for example, diamines such as diphenyl-p-phenylenediamine. Amounts of antiozonants can range from about 1 to about 5 phr and all subranges therebetween. Amounts of fatty acids, e.g., stearic acid, can range from about 0.5 to about 3 phr and all subranges therebetween. Amounts of zinc oxide can range from about 2 to about 5 phr and all subranges therebetween. Amounts of waxes can range from about 1 to about 5 phr. Typical amounts of peptizers can range from about 0.1 to about 1 phr and all subranges therebetween. Such peptizers include, for example, pentachlorothiophenol and dibenzamidodiphenyl disulfide.

The rubber compositions of this invention are useful when manufactured into articles such as, for example, tires, motor mounts, rubber bushings, power belts, printing rolls, rubber shoe heels and soles, rubber floor tiles, caster wheels, elastomer seals and gaskets, conveyor belt covers, hard rubber battery cases, automobile floor mats, mud flap for trucks, ball mill liners, windshield wiper blades and the like. In one embodiment, the rubber compositions are advantageously used in a tire as a component of any or all of the thermosetting rubber-containing portions of the tire. These include the tread, sidewall, and carcass portions intended for, but not exclusive to, a truck tire, passenger tire, off-road vehicle tire, vehicle tire, high speed tire, and motorcycle tire that also contain many different reinforcing layers therein. Such rubber or tire tread compositions may be used for the manufacture of tires or for the re-capping of worn tires. In one embodiment of the invention, the rubber composition has a reinforcing index (ratio of 300% to 100% modulus) of at least about 4. In another embodiment, the index is at least 4.5. In a third embodiment, the composition has a Delta G' value of less than 6.0. In yet another embodiment, the composition has a tangent delta max value of less than 0.250.

The following non-limiting examples are intended to further illustrate the present invention and are not intended to limit the scope of the invention in any manner.

EXAMPLE 1

Preparation of Styrenic Thioether Triethoxysilane Reaction Product of Mercaptopropyltriethoxysilane and Vinylbenzylchloride Into a 2 liter three-necked round bottom flask equipped with a mechanical stirrer, condenser, temperature probe and addition funnel 4-vinylbenzylchloride (216.8 g, 1.42 moles) was added over a period of 1.5 hours to a mixture of mercaptopropyltriethoxysilane (338.3 g, 1.42 moles) and sodium ethoxide solution (21 wt. % in ethanol, 459.9 g, 1.42 moles). The resulting mixture was left to stir for an hour at room temperature, filtered and stripped of ethanol at 70° C. under full vacuum using a short path distillation head. 479.2 g of product was recovered with a yield of about 95%.

EXAMPLE 2

Preparation of a Bis-styrenic Amino Triethoxysilane Reaction Product of Aminopropyltriethoxysilane and Vinylbenzylchloride Into a 1 liter three-necked round bottom flask, equipped with a mechanical stirrer, addition funnel, and temperature probe 4-vinylbenzylchloride (201.4 g, 1.3 moles) was added over a period of 16 hours to a mixture of aminopropyltriethoxysilane (165.7 g, 0.74 moles) and triethylamine (137.0 g, 1.3 moles) at 70° C. The resulting solution was cooled to ambient temperature for 16 hours, filtered and subsequently stripped of triethylamine under full vacuum and ambient temperature using a short path distillation head. 252.0 g of product was recovered having a yield of about 100%.

EXAMPLE 3

Preparation of Triethoxysilane Derived by Hydrosilylation of Di-iso-propenylbenzene Step 1. Trichlorosilane (2042.1 g, 15.07 moles) was added over a period of 6 hours to a mixture of diisopropylbenzene (3762.0 g, 23.77 moles), hexane (2500 mL), platinum (0)-2, 4,6,8-tetramethyl-2,4,6,8-tetravinylcyclotetrasiloxane complex (11.2 g of a 0.104 M solution) and Ionol (butylated hydroxy toluene) (2.8 g) at 55° C. The addition was performed in two batches; each in a 5 liter 3 necked round bottom flask equipped with a magnetic stir bar, condenser, heating mantle and temperature probe. The resulting material from both batches was combined and then stripped of hexane under full vacuum. The remainder was distilled at 150° C. under full vacuum using a short path distillation head. 1616.2 grams of 1-(1-methyl-2-trichlorosilylethyl)-3-propenylbenzene were recovered. Yield=55%.

Step 2 Into a 5 liter three-necked round bottom flask equipped with a magnetic stir bar, heating mantle and temperature probe 1-(1-methyl-2-trichlorosilylethyl)-3-propenylbenzene (1616.2 g, 5.5 moles) was added over a period of 4 hours to a mixture of triethylorthoformate (2241.0 g, 15.1 moles), Ionol (3 g) and hydrochloric acid (0.1 g of 37% aqueous solution) at 50° C. The reaction vessel was heated at 50° C. for 64 hours. Additional triethylorthoformate (730 g, 4.9 moles) was charged to the reaction vessel after distilling off approximately 700 grams of low boiling material. The reaction vessel was heated 8 hours at 50° C. before distillation of the product, which is a mixture of 1-(1-methyl-2-triethoxysilylethyl)-3-propenylbenzene and 1-(1-methyl-2-diethoxychlorosilylethyl)-3-propenylbenzene. The material was distilled using a kugelrohr apparatus at 120° C. and full vacuum. 1110.8 grams of material were recovered. Yield=68%.

Step 3 Into a 5 liter three-necked round bottom flask equipped with a mechanical stirrer, addition funnel and temperature probe ethanol (275.8 g, 6.0 moles) was added over a period of 2 hours to the mixture of 1-(1-methyl-2-triethoxysilylethyl)-3-propenylbenzene and 1-(1-methyl-2-diethoxychlorosilylethyl)-3-propenylbenzene (992.5 g), triethylamine (509.6 g, 5.03 moles), and hexane (4000 mL) at 5° C. The resulting mixture was filtered and stripped of hexane, triethylamine and ethanol, using a short path distillation head. 901.0 g of 1-(1-methyl-2-triethoxysilylethyl)-3-propenylbenzene was recovered.

EXAMPLE 4

Preparation of the Isoproxy Derivative of a Bis-styrenic Amino Triethoxysilane Reaction Product of Aminopropyltriethoxysilane and Vinylbenzylchloride Into a 1 liter three-necked round bottom flask, equipped with a magnetic stirrer, addition funnel, and temperature probe under nitrogen 4-vinylbenzylchloride (216 g, 1.42 moles) was added over a period of 16 hours to a mixture of aminopropyltri-iso-propoxysilane (373 g, 1.42 moles) and triethylamine (143 g, 1.41 moles) at room temperature, which rose to 80° C. by exothermic heat of reaction, over 2 hours. Gas chromatography of the reaction mixture after cooling showed unreacted starting aminosilane, the desired mono-adduct styrenic silane, and the bis-adduct styrenic silane, (i-PrO)$_3$Si—CH$_2$CH$_2$CH$_2$N(CH$_2$—C$_6$H$_4$—CH=CH$_2$)$_2$.

COMPARATIVE EXAMPLE 1

Attempted Synthesis Mono-adduct of Mercaptopropyltriethoxysilane with Divinylbenzene An attempt to synthesize the mono-adduct of mercaptopropyltriethoxysilane with divinylbenzene with no base resulted in an extremely sluggish reaction with by-products. However, a small amount of the desired styrenic silane was formed and detected by gas chromatography before the experiment was discontinued. In the experiment, to a 2 L round bottom flask equipped with an addition funnel, magnetic stirrer and condenser were added 400 ml of hexane and 222.1 grams of divinylbenzene (1.705 moles) under nitrogen atmosphere. 336 g (1.53 moles) of gamma-mercaptopropyltriethoxysilane were charged to the addition funnel and added dropwise, first at room temperature, then at 50° C. No reaction occurred. The reaction mixture was heated to 80° C. for 9.5 days and a trace of the mono-adduct styrenic silane was observed by gas chromatography.

EXAMPLE 5

The Use of Silanes of Examples 1 to 3 in Low Rolling Resistant Tire Tread Formulations A general procedure was followed for compounding and testing the silanes in (1) a silica-filled synthetic rubber (Procedure A); (2) a silica-filled natural rubber (NR) (Procedure B) and (3) carbon-black filled tread compounds (Procedure C). Procedures A-C are set forth below.

Procedure A

A model low rolling resistance passenger tire tread formulation as described in Table A below and this mix procedure were used to evaluate of silica filled tire treads of synthetic rubber containing the silanes of Examples 1 to 3. The tire tread containing the silane of Example 1 was mixed as follows in a "B" BANBURY(™) (Farrell Corp.) mixer with a 103 cu. in. (1690 cc) chamber volume. The mixing of the rubber masterbatch was done in two steps. The mixer was turned on with the mixer at 120 rpm and the cooling water on full. The rubber polymers were added to the mixer and ram down mixed for 30 seconds. Half of the silica and all of the silane with approximately 35-40 grams of this portion of silica in an ethylenevinylacetate (EVA) bag were added and ram down mixed for 30 seconds. The remaining silica and the oil in an EVA bag were next added and ram down mixed for 30 seconds. The mixer throat was thrice dusted down, and the mixture ram down mixed for 15 seconds each time. The mixer's mixing speed was increased to 160 or 240 rpm, as required to raise the temperature of the rubber masterbatch to between 160° C. and 165° C. in approximately one minute. The masterbatch was dumped (removed from the mixer); a sheet was formed on a roll mill set at about 50° C. to 60° C., and then allowed to cool to ambient temperature.

The rubber masterbatch was added to the mixer with the mixer at 120 rpm and cooling water turned on full and ram down mixed for 30 seconds. The remainder of the ingredients was added and ram down mixed for 30 seconds. The mixer throat was dusted down, the mixer speed increased to 160 or 240 rpm so that the contents reached a temperature between 160° C. and 165° C. in approximately two minutes. The rubber masterbatch was mixed for eight minutes, and the speed of the BANBURY mixer as adjusted to maintain the temperature between 160° C. and 165° C. The masterbatch was dumped (removed from the mixer); a sheet was formed on a roll mill set at about 50° C. to 60° C., and then allowed to cool to ambient temperature.

The rubber masterbatch and the curatives were mixed on a 6-in. diameter by 13-inch long (15 cm by 33 cm) two-roll mill that was heated to between 50° C. and 60° C. The sulfur and accelerators were added to the rubber masterbatch and thoroughly mixed on the roll mill and allowed to form a sheet. The sheet was cooled to ambient conditions for 24 hours before it was cured. The rheological properties were measured on a Monsanto R-100 Oscillating Disk Rheometer and a Monsanto M1400 Mooney Viscometer. The specimens for measuring the mechanical properties were cut from 6-mm plaques cured for 35 minutes at 160° C. or from 2-mm plaques cured for 25 minutes at 160° C.

The silanes of Examples 2 and 3 were also compounded into the tire tread formulation according to the above procedure A.

Procedure B

A model low rolling resistance passenger tire tread formulation as described in Table B and a mix procedure were used to prepare silica filled tire treads of natural rubber containing the silanes of Examples 1 to 3. The tire tread containing the silane of Example 1 was mixed as follows in a "B" BANBURY(™) (Farrell Corp.) mixer with a 103 cu. in. (1690 cc) chamber volume. The mixing of the rubber masterbatch was done in two steps. The mixer was turned on with the mixer at 77 rpm and the cooling water at 140° F. (60° C.) on full. The rubber polymers were added to the mixer and ram down mixed for 30 seconds. Half of the silica and all of the silane with approximately 35-40 grams of this portion of silica in an ethylvinylacetate (EVA) bag were added and ran down mixed for 30 seconds. The remaining silica and the oil in an EVA bag were next added and ram down mixed for 30 seconds. The mixer throat was thrice dusted down, and the mixture ram down mixed for 20 seconds each time. The temperature of the rubber masterbatch was allowed to rise to 300° F. (150° C. ), with increased RPM if needed. The masterbatch was immediately dumped (removed from the mixer), a sheet was formed on a roll mill set at about 170-180° F. (75-80° C. and then allowed to cool to ambient temperature.

The rubber masterbatch was added to the mixer with the mixer at 77 rpm and cooling water at 140° F. (60° C.) and ram down mixed for 30 seconds. The remainder of the ingredients was added and ram down mixed for 60 seconds. The mixer throat was dusted down; the temperature increased to 300° F. (150° C.), using higher rpm if needed. The compound was mixed for 3 minutes at 290 to 300° F. (145-150° C.). The compound was dumped (removed from the mixer), a sheet was formed on a roll mill set at about 170-180° F. (75-80° C.) and then allowed to cool to ambient temperature.

The rubber masterbatch and the curatives were mixed on a 6-in. diameter by 13-inch long (15 cm by 33 cm) two-roll mill that was heated to between 50 to 60° C. The sulfur and accelerators were added to the rubber masterbatch and thoroughly mixed on the roll mill and allowed to form a sheet. The sheet was cooled to ambient conditions for 24 hours before it was cured. The rheological properties were measured on a Monsanto R-100 Oscillating Disk Rheometer and a Monsanto M1400 Mooney Viscometer. The specimens for measuring the mechanical properties were cut from 6-mm plaques cured for 35 minutes at 160° C. or from 2-mm plaques cured for 25 minutes at 160° C.

The silanes of Examples 2 and 3 were also compounded into the tire tread formulation according to the above procedure B.

Procedure C

A model low rolling resistance passenger tire tread formulation as described in Table C and a mix procedure were used to prepare carbon black filled tire tread of natural rubber containing the silanes of Examples 1 to 3. The tire tread containing the silane of Example 1 was mixed as follows in a "B" BANBURY (Farrell Corp.) mixer with a 103 cu. in. (1690 cc) chamber volume. The mixing of the rubber masterbatch was done in two steps. The mixer was turned on with the mixer at 77 rpm and the cooling water at 140° F. (60° C.) on full. The rubber polymers were added to the mixer and ram down mixed for 30 seconds. All of the carbon black and all of the oil were added and ram down mixed for 60 seconds. The mixer throat was dusted down, and the mixture ram down mixed for 20 seconds. The mixer throat was dusted down a second time, and the temperature of the rubber masterbatch was allowed to rise to 300° F. (150° C.), with increased RPM if needed. The masterbatch was immediately dumped (removed from the mixer), a sheet was formed on a roll mill set at about 170-180° F. (75-80° C.) and then allowed to cool to ambient temperature.

The rubber masterbatch was added to the mixer with the mixer at 77 rpm and cooling water at 140° F. (60° C.) and ram down mixed for 30 seconds. The remainder of the ingredients was added and ram down mixed for 60 seconds. The mixer throat was dusted down; the temperature increased to 300° F. (150° C.), using higher rpm if needed. The compound was dumped (removed from the mixer), a sheet was formed on a roll mill set at about 170-180° F. (75-80° C.) and then allowed to cool to ambient temperature.

The rubber masterbatch and the curatives were mixed on a 6-in. diameter by 13-inch long (15 cm by 33 cm) two-roll mill that was heated to between 50 and 60° C. The sulfur and accelerators were added to the rubber masterbatch and thoroughly mixed on the roll mill and allowed to form a sheet. The sheet was cooled to ambient conditions for 24 hours before it was cured. The rheological properties were measured on a Monsanto R-100 Oscillating Disk Rheometer and a Monsanto M1400 Mooney Viscometer. The specimens for measuring the mechanical properties were cut from 6-mm plaques cured for 35 minutes at 160° C. or from 2-mm plaques cured for 25 minutes at 160° C.

The silanes of Examples 2 and 3 were also compounded into the tire tread formulation according to the above procedure C.

The silanes from Examples 1 to 3 were compounded into the tire tread formulation of Formulations A, B, or C as follows, according to the above corresponding respective procedures A, B, and C. Formulation A is passenger car tire SBR based, Formulation B is Truck tire NR based. The performance of the silanes prepared in Examples 1 to 3 was compared to the performance of no silane coupling agent (Silane α), standard polysulfide silanes, commonly used in the prior art, bis-(3-triethoxysilyl-1-propyl) tetrasulfide (TESPT, Silane β), and bis-(triethoxysilylpropyl) disulfide (TESPD, Silane γ). The results of these procedure and tests are tabulated below in Table 2.

TABLE A

Model Low Rolling Resistance Tread Formulation A

| PHR | Ingredient |
|---|---|
| 75 | sSBR (12% styrene, 46% vinyl, $T_g$: 42° C.) |
| 25 | BR (98% cis, $T_g$: 104° C.) |
| 80 | Silica (150-190 m$^2$/gm, ZEOSIL 1165MP, Rhone-Poulenc) |
| 32.5 | Aromatic process oil (high viscosity, Sundex 8125, Sun) |
| 2.5 | Zinc oxide (KADOX 720C, Zinc Corp.) |
| 1 | Stearic acid (INDUSTRENE, Crompton) |
| 2 | 6PPD antiozonant (SANTOFLEX 6PPD, Flexsys) |
| 1.5 | Microcrystalline wax (M-4067, Schumann) |
| 3 | N330 carbon black (Engineered Carbons) |
| 1.4 | Sulfur (#104, Sunbelt) |
| 1.7 | CBS accelerator (SANTOCURE, Flexsys) |
| 2 | DPG accelerator (PERKACIT DPG-C, Flexsys) |

TABLE B

Model Low Rolling Resistance Tread Formulation B

| PHR | Ingredient |
|---|---|
| 100 | SMR-L NR |
| 3 | N-110 Carbon Black |
| 50 | Silica (150-190 m$^2$/gm, ZEOSIL 1165MP, Rhone-Poulenc) |
| 5 | Aromatic process oil (high viscosity, Sundex 8125, Sun) |
| 4 | Zinc oxide (KADOX 720C, Zinc Corp.) |
| 2 | Stearic acid (INDUSTRENE, Crompton Corp.) |
| 2 | Naugard Q antioxidant (polymerized dihydrotrimethylquinoline, Crompton Corp.) |
| 2.5 | N-1,3-dimethylbutyl-N'-phenyl-p-phenylenediamine (Flexzone 7P antiozonant, Crompton Corp.) |
| 1 | Sunproof Improved wax (Crompton Corp.) |
| 1.4 | Rubbermakers sulfur 104 (Sunbelt) |
| 1.6 | TBBS accelerator (Delac NS, Crompton Corp.) |
| 2 | DPG accelerator (PERKACIT DPG-C, Flexsys) |

TABLE C

Model Low Rolling Resistance Tread Formulation C

| PHR | Ingredient |
|---|---|
| 100 | SMR-L NR |
| 50 | N-110 Carbon Black |
| 5 | Aromatic process oil (high viscosity, Sundex 8125, Sun) |
| 4 | Zinc oxide (KADOX 720C, Zinc Corp.) |
| 2 | Stearic acid (INDUSTRENE, Crompton Corp.) |
| 2 | Naugard Q antioxidant (polymerized dihydrotrimethylquinoline, Crompton Corp.) |
| 2.5 | N-1,3-dimethylbutyl-N'-phenyl-p-phenylenediamine (Flexzone 7P antiozonant, Crompton Corp.) |
| 1 | Sunproof Improved wax (Crompton Corp.) |
| 1.4 | Rubbermakers sulfur 104 (Sunbelt) |
| 1.6 | TBBS accelerator (Delac NS, Crompton Corp.) |

The following tests were conducted for the treads prepared in each of the above formulations A-C with the following methods (in all examples): Mooney Scorch @ 135E C (ASTM Procedure D1646); Mooney Viscosity @ 100° C. (ASTM Procedure D1646); Oscillating Disc Rheometer (ODR) @ 149° C.; 1°arc, (ASTM Procedure D2084); Physical Properties, cured t90 @ 149° C. (ASTM Procedures D412 and D224) (G' and G" in dynes/cm$^2$); DIN Abrasion, mm$^3$ (DIN Procedure 53516); and Heat Build (ASTM Procedure D623). The results of these tests are set forth below in Table 2.

TABLE 2

Performance of Representative Silanes in a Model Low Rolling Resistance Tire Formulation

| Silane | α | β TESPT | β TESPT | γ TESPD | γ TESPD | Ex. 1 | Ex. 1 | Ex. 2 | Ex. 3* | Ex. 3 |
|---|---|---|---|---|---|---|---|---|---|---|
| Amount (phr) | 0 | 7 | 4 | 6.22 | 3.54 | 9.42 | 5.29 | 6.27 | 2.76 | 5.3 |
| Procedure | C | A | B | A | B | A | B | B | B | B |
| Mooney Viscosity (ML 1 + 4) | 60 | 71 | 49 | 68 | 54 | 65 | 51 | 48 | 52 | 43 |
| 300% Modulus (KPSI) | 2100 | 2040 | 2110 | 1365 | 1945 | 1320 | 1555 | 1780 | 1550 | 1223 |
| Ratio - 300% to 100% modulus | 5.2 | 6.6 | 4.7 | 5.6 | 4.4 | 5.3 | 4.6 | 4.7 | 4.8 | 5.0 |
| Delta G' | 6.1 | 0.85 | 2.65 | 1.5 | 3.1 | 1.19 | 2.7 | 1.9 | 3.41 | 2.5 |
| Tangent delta max | 0.272 | 0.155 | 0.18 | 0.203 | 0.2 | 0.18 | 0.208 | 0.2 | 0.180 | 0.182 |

*The silane used was the intermediate formed in step 2 of Example 3.

Although the invention has been described in its preferred embodiments with a certain degree of particularity, obviously many changes and variations are possible therein and will be apparent to those skilled in the art after reading the foregoing description. It is therefore to be understood that the present invention may be presented otherwise than as specifically described herein without departing from the spirit and scope thereof.

What is claimed is:

1. A silane composition comprising

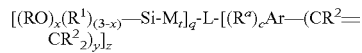

wherein R and $R^1$ are independently a hydrocarbon group of from 1 to about 20 carbon atoms; $R^2$ are each independently hydrogen or a hydrocarbon group of from 1 to about 20 carbon atoms; M is a divalent hydrocarbon connecting group of from 1 to about 20 carbon atoms to link the silicon atom and the L group; L is a heteroatom linking group selected from the group consisting of —O—, —S—, —$NR^3$— wherein $R^3$ is a bond or a hydrocarbon group of from 1 to about 20 carbon atoms; $R^a$ is an alkylene group of 1 to 12 carbon atoms; Ar is a substituted or unsubstituted aromatic group; q is an integer of 1 to 4; t and c are each independently 0 or 1; and x, y and z are each independently integers of 1 to 3, inclusive.

2. The silane composition of claim 1, wherein x is 1, R and $R^1$ are independently methyl, ethyl, propyl, isopropyl, butyl, tert-butyl, isobutyl, pentyl, dodecyl or phenyl and Ar is a benzene group.

3. The silane composition of claim 1, wherein x is 2, R and $R^1$ are independently methyl, ethyl, propyl, isopropyl, butyl, tert-butyl, isobutyl, pentyl, dodecyl or phenyl and Ar is a benzene group.

4. The silane composition of claim 1, wherein the heteroatom linking group is —$NR^3$—.

5. The silane composition of claim 1, wherein x is 3, R is independently methyl, ethyl, propyl, isopropyl, butyl, tert-butyl, isobutyl, pentyl, dodecyl or phenyl and Ar is a benzene group.

6. The silane composition of claim 5, wherein the heteroatom linking group is —$NR^3$—.

7. A process for the preparation of a silane composition comprising

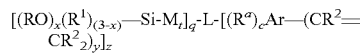

wherein R and $R^1$ are independently a hydrocarbon group of from 1 to about 20 carbon atoms; $R^2$ are each independently hydrogen or a hydrocarbon group of from 1 to about 20 carbon atoms; M is a divalent hydrocarbon connection group of from 1 to about 20 carbon atoms to link the silicon atom and the L group; L is a heteroatom linking group selected from the group consisting of —O—, —S—, —$NR^3$— wherein $R^3$ is a bond or a hydrocarbon group of from 1 to about 20 carbon atoms; $R^a$ is an alkylene group of 1 to 12 carbon atoms; Ar is a substituted or unsubstituted aromatic group; q is an integer of 1 to 4; t and c are each independently 0 or 1; and x, y and z are each independently integers of 1 to 3, inclusive, with the proviso that t is 1 when L is a heteroatom group; wherein said silane composition is prepared by:

reacting at least one silane reactant represented by the general formula

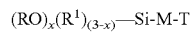

wherein M is a divalent hydrocarbon connecting group of from 1 to about 20 carbon atoms to link the silicon atom and the T group; T is a compound selected from the group consisting of a mercapto compound, a hydroxy compound and an amine of the general formula —$NR^4R^5$ wherein $R^4$ and $R^5$ are independently hydrogen or a hydrocarbon group of from 1 to about 20 carbon atoms and wherein at least one of $R^4$ and $R^5$ are hydrogen and x is an integer of 1 to 3, inclusive; with at least one unsaturated reactant represented by the general formula

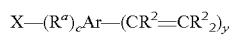

wherein X is an anion of an organic or inorganic acid; $R^a$ is an alkyl group of 1 to 12 carbon atoms; Ar is a substituted or unsubstituted aromatic group; $R^2$ are each independently hydrogen or a hydrocarbon group of from 1 to about 20 carbon atoms; c is 0 or 1 and y is an integer of 1 to 3; in the presence of an effective amount of at least one base.

8. The process of claim 7, wherein the base is added to the silane reactant to form a mixture and then reacting the mixture of silane reactant and base with the unsaturated reactant.

9. The process of claim 7, wherein the base is an alkoxide of an alkali metal or alkaline earth metal.

10. The process of claim 9, wherein the alkoxides are selected from the group consisting of sodium methoxide, sodium ethoxide, calcium methoxide, calcium ethoxide, sodium propoxide, sodium tert-butoxide, potassium propoxide, potassium tert-butoxide, lithium methoxide, lithium ethoxide, lithium propoxide, lithium tert-butoxide and combinations thereof.

11. The process of claim 7, wherein the base is a tertiary amine.

12. The process of claim 11, wherein the tertiary amine is a trialkylamine.

13. The process of claim 12, wherein the trialkylamine is triethylamine.

14. The process of claim 7, wherein the silane reactant is reacted with the unsaturated reactant in a molar ratio of about 1:0.1 to about 1:10 of silane reactant to unsaturated reactant.

15. The process of claim 7, wherein the silane reactant is reacted with the unsaturated reactant in a molar ratio of about 1:0.5 to about 1:2 of silane reactant to unsaturated reactant.

16. The process of claim 7, wherein the effective amount of the base is about 1 to about 10 molar equivalents of base to the silane reactant.

17. The process of claim 7, wherein the effective amount of the base is about 1.1 to about 2 molar equivalents of base to the silane reactant.

18. The process of claim 7, wherein x is 1, R and $R^1$ are independently methyl, ethyl, propyl, isopropyl, butyl, tert-butyl, isobutyl, pentyl, dodecyl or phenyl and Ar is a benzene group.

19. The process of claim 7, wherein x is 2, R and $R^1$ are independently methyl, ethyl, propyl, isopropyl, butyl, tert-butyl, isobutyl, pentyl, dodecyl or phenyl and Ar is a benzene group.

20. The process of claim 18, wherein the heteroatom linking group is an amine of the general formula —$NR^4R^5$.

21. The process of claim 19, wherein the heteroatom linking group is an amine of the general formula —$NR^4R^5$.

22. The process of claim 7, wherein x is 3, R is independently methyl, ethyl, propyl, isopropyl, butyl, tert-butyl, isobutyl, pentyl, dodecyl or phenyl and Ar is a benzene group.

23. The process of claim 22, wherein the heteroatom linking group is an amine of the general formula —$NR^4R^5$.

24. The process of claim 7, further comprising a solvent.

25. The process of claim 24, wherein the solvent is an alcohol.

26. The process of claim 7, wherein the silane reactant is selected from the group consisting of aminosilanes, mercaptosilanes and mixtures thereof and the unsaturated reactant is selected from the group consisting of vinylbenzylchloride, divinylbenzylchloride and mixtures thereof.

27. The process of claim 7, wherein the silane reactant is selected from the group consisting of 3-aminopropyltrimethoxysilane, 3-aminopropyldimethylmethoxysilane, 3-aminopropylmethyldimethoxysilane, 3-(aminopropyl)ethyldimethoxysilane, 3-aminopropyltriethoxysilane, 3-aminopropyldimethylethoxysilane, 3-aminopropylphenyldimethoxysilane, 2-aminoethyltriethoxysilane, 4-aminobutyltriethoxysilane, 4-aminobutyltrimethoxysilane, 4-aminobutylmethyldimethoxysilane, 4-(trimethoxysilyl)-2-butanamine, 3-[diethoxy(hexyloxy)silyl]-1-propanamine, 3-[tris(pentyloxy)silyl]-1-propanamine, 3-[tris(2,2,2-trifluoroethoxy)silyl]-1-propanamine, 3-[tris[2-(2-phenoxyethoxy)ethoxy]silyl]-1-propanamine, 3-[tris[(2-ethylhexyl)oxy]silyl]-1-propaneamine, 3-[tris(hexyloxy) silyl]-1-propanamine, 3-triisopropoxysilylpropylamine, 3-[tris(3-methylbutoxy)silyl]-1-propanamine, 3-[tris(2-ethoxyethoxy)silyl]-1-propanamine, 3-[bis( 1,1-dimethylethoxy)methoxysilyl]-1-propanamine, 3[(1,1-dimethylethoxy)diethoxysilyl]-1-propanamine, 3-[(1,1-dimethylethoxy)dimethoxysilyl]-1-propanamine, 3-(trimethoxysilyl)-1-pentanamine, 4-amino-3,3-dimethylbutyltrimethoxysilane, 4-amino-3,3-dimethylbutyltriethoxysilane, mercaptopropyltriethoxysilane and mixtures thereof and the unsaturated reactant is selected from the group consisting of vinylbenzylchloride, divinylbenzylchloride and mixtures thereof.

28. A process for the preparation of a silane composition comprising reacting at least one silicon hydride represented by the general formula $R_bHSiZ_{3-b}$ wherein each $R_b$ is independently a hydrocarbon group of from 1 to about 20 carbon atoms; Z is a halogen atom and b is from 0 to 3, with at least one unsaturated reactant represented by the general formula

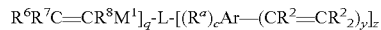

wherein Ar is a substituted or unsubstituted aromatic group; $R^2$ are each independently hydrogen or a hydrocarbon group of from 1 to about 20 carbon atoms; $R^6$, $R^7$ and $R^8$ are each independently hydrogen or a hydrocarbon group of from 1 to about 6 carbon atoms, $M^1$ is a bond or divalent hydrocarbon connecting group from 1 to about 18 carbon atoms and wherein $R^6$, $R^7$ and $R^8$ and $M^1$ have a combined total of carbon atoms of no more that about 18; L is a heteroatom linking group selected from the group consisting of —O—, —S—, —$NR^3$— wherein $R^3$ is a bond or a hydrocarbon group of from 1 to about 20 carbon atoms; $R^a$ is an alkylene group of 1 to 12 carbon atoms; c is 0 or 1; y and z are independently integers of 1 to 3; and q is an integer of 1 to 4, in the presence of at least one hydrosilating catalyst.

29. The process of claim 28, wherein b is 0 and Z is chloro for the silicon hydride.

30. The process of claim 28, wherein b is 0 and Z is chloro for the silicon hydride and s is 1 for the unsaturated reactant.

31. The process of claim 28, wherein the hydrosilating catalyst is $H_2PtCl_6$, $RhCl_3$, $Rh(PPh_3)_3$, Cl, Speier's catalyst, Karstedt's catalyst, Ashby's catalyst or Lamoreoux's catalyst.

32. The process of claim 28, wherein the hydrosilating catalyst is a free radical initiator.

33. The process of claim 28, further comprising reacting the product obtained from the reaction when b is 0, 1 or 2 for the silicon hydride reactant with a first ether-forming agent to provide alkoxy groups attached to the silicon atom.

34. The process of claim 28, further comprising reacting the product obtained when b is 0 and Z is chloro for the silicon hydride reactant with a first ether-forming agent to provide alkoxy groups attached to the silicon atom.

35. The process of claim 34, wherein the first ether-forming agent is a trialkylorthoformate.

36. The process of claim 35, wherein the trialkylorthoformate is triethylorthoformate.

37. The process of claim 34, further comprising adding a second ether-forming agent.

38. The process of claim 37, wherein the second ether-forming agent is an alcohol.

39. The process of claim 28, wherein the concentration of the hydrosilating catalyst is about 0.1 ppm to about 1 part.

40. The process of claim 28, wherein the concentration of the hydrosilating catalyst is about 10 ppm to about 1000 ppm.

41. The process of claim 28, wherein the silicon hydride reactant is reacted with the unsaturated reactant in a molar ratio of silicon hydride reactant to unsaturated reactant of about 1:100 to about 100:1.

42. The process of claim 28, wherein the silicon hydride reactant is reacted with the unsaturated reactant in a molar ratio of silicon hydride reactant to unsaturated reactant of about 1:10 to about 10:1.

43. The process of claim 28, wherein the silicon hydride reactant is reacted with the unsaturated reactant in a molar ratio of silicon hydride reactant to unsaturated reactant of about 2:1 to about 1:2.

44. A rubber comprising (a) a rubber component; (b) a filler; and (c) a silane compositioin comprising

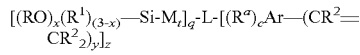

wherein R and $R^1$ are independently a hydrocarbon group of from 1 to about 20 carbon atoms; $R^2$ are each independently hydrogen or a hydrocarbon group of from 1 to about 20 carbon atoms; M is a divalent hydrocarbon connecting group of from 1 to about 20 carbon atoms to link the silicon atom and the L group; L is a heteroatom linking group selected from the group consisting of —O—, —S—, —$NR^3$— wherein $R^3$ is a bond or a hydrocarbon group of from 1 to about 20 carbon atoms; $R^a$ is an alkylene group of 1 to 12 carbon atoms; Ar is a substituted or unsubstituted aromatic group; q is an integer of 1 to 4; t and c are each independently 0 or 1; and x, y and z are each independently integers of 1 to 3, inclusive, with the proviso that t is 1 when L is a heteroatom group.

45. The rubber composition of claim 44, wherein the composition has a reinforcing index of at least about 4.

46. The rubber composition of claim 44, wherein the composition has a Delta G' value of less than 6.

47. The rubber composition of claim 44, wherein the composition has a tangent delta max value of less than 0.250.

48. The rubber composition of claim 44, wherein the filler is one or more fillers selected from the group consisting of silica fillers, carbon black fillers and mixtures thereof.

49. The rubber composition of claim 44, wherein the filler is a silica Filler selected from the grouop consisting of silica, precipitated silica, amorphous silica, vitreous silica, fumed silica, fused silica, synthetic silicate, alkaline earth metal silicate, highly dispersed silicate and mixtures thereof.

50. The rubber composition of claim 44, wherein the silane composition X is 1, R and $R^1$ are independently methyl, ethyl, propyl, isopropyl, butyl, tert-butyl, isobutyl, pentyl, dodecyl or phenyl and Ar is a benzene group.

51. The rubber composition of claim 44, wherein the silane composition x is 2, R and $R^1$ are independently methyl, ethyl, propyl, isopropyl, tert-butyl, isobutyl, pentyl, dodecyl or phenyl and Ar is a benzene group.

52. The rubber composition of claim 44, wherein the heteroatom linking group is –$NR^3$–.

53. The rubber composition of claim 44, wherein the silane composition x is 3, R is independently methyl, ethyl, propyl, isopropyl, butyl, tert-butyl, isobutyl, pentyl, dodecyl, or phenyl and Ar is a benzene group.

54. The rubber composition of claim 53, wherein the heteroatom linking group is –$NR^3$–.

55. The rubber composition of claim 44, wherein the silane composition is present in an amount of about 0.05 to about 25 phr.

56. The rubber composition of claim 55, wherein the silane composition is present in an amount of about 1 to about 10 phr.

57. A tire tread comprising the rubber composition of claim 44.

58. A tire having a tread comprising the rubber composition of claim 57.

59. A tire tread comprising the rubber composition of claim 44, wherein said silane composition is present in a sufficient amount to maximize the ratio of 300% elongation modulus to the 100% elongation modulus.

60. A process for preparing a rubber composition Comprising ading to a rubber composition reaction forming mixture an effective amount of at least one silane composition of the general formula

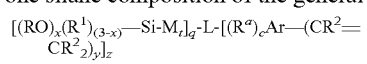

wherein R and $R^1$ are independently a hydrocarbon group of from 1 to about 20 carbon atoms; $R^2$ are each independently hydrogen or a hydrocarbon group of from 1 to about 20 carbon atoms; M is a divalent hydrocarbon connecting group of from 1 to about 20 carbon atoms to link the silicon atom and the L group; L is a heteroatom linking group selected from the group consisting of —O—, —S—, —$NR^3$— wherein $R^3$ is a bond or a hydrocarbon group of from 1 to about 20 carbon atoms; $R^a$ is an alkylene group of 1 to 12 carbon atoms; Ar is a substituted or unsubstituted aromatic group; q is an integer of 1 to 4; t and c are each independently 0 or 1; and x, y and z are each independently integers of 1 to 3, inclusive, with the proviso that t is 1 when L is a heteroatom group.

61. The process of claim 60, wherein x is 1, R and $R^1$ are independently methyl, ethyl, propyl, isopropyl, butyl, tert-butyl, isobutyl, pentyl, dodecyl or phenyl and Ar is a benzene group.

62. The process of claim 61, wherein xis 2, R and $R^1$ are independently methyl, ethyl, propyl, isopropyl, butyl, tert-butyl, isobutyl, pentyl, dodecyl or phenyl and Ar is a benzene group.

63. The process of claim 62, wherein the Heteroatom linking group is –$NR^3$–.

* * * * *